United States Patent
Yotsuya et al.

(10) Patent No.: US 8,604,212 B2
(45) Date of Patent: Dec. 10, 2013

(54) ANTI-SHOCK AGENT COMPRISING DIAMINOTRIFLUOROMETHYLPYRIDINE DERIVATIVE

(75) Inventors: Shuichi Yotsuya, Shiga (JP); Hiroshi Shikama, Shiga (JP)

(73) Assignee: Ishihara Sangyo Kaisha, Ltd., Osaka-shi (JP)

(*) Notice: Subject to any disclaimer, the term of this patent is extended or adjusted under 35 U.S.C. 154(b) by 0 days.

(21) Appl. No.: 13/320,570

(22) PCT Filed: May 17, 2010

(86) PCT No.: PCT/JP2010/058310
§ 371 (c)(1),
(2), (4) Date: Nov. 15, 2011

(87) PCT Pub. No.: WO2010/137484
PCT Pub. Date: Dec. 2, 2010

(65) Prior Publication Data
US 2012/0059039 A1    Mar. 8, 2012

(30) Foreign Application Priority Data

May 28, 2009 (JP) .................................. 2009-129578

(51) Int. Cl.
*C07D 409/00* (2006.01)
*C07D 213/00* (2006.01)
*A61K 31/44* (2006.01)

(52) U.S. Cl.
USPC ......... 546/281.4; 546/308; 514/336; 514/353

(58) Field of Classification Search
USPC .................. 514/336, 353; 546/281.4, 308
See application file for complete search history.

(56) References Cited

U.S. PATENT DOCUMENTS

| | | | |
|---|---|---|---|
| 5,229,403 A | 7/1993 | Haga et al. | |
| 5,260,320 A | 11/1993 | Haga et al. | |
| 5,348,967 A | 9/1994 | Haga et al. | |
| 5,492,908 A | 2/1996 | Haga et al. | |
| 6,197,796 B1 | 3/2001 | Ogura | |
| 6,635,665 B2 | 10/2003 | Morino et al. | |
| 6,653,333 B2 | 11/2003 | Yotsuya et al. | |
| 6,664,279 B2 | 12/2003 | Yotsuya et al. | |
| 2002/0019416 A1 | 2/2002 | Fukami et al. | |
| 2004/0110825 A1 | 6/2004 | Loh et al. | |

FOREIGN PATENT DOCUMENTS

| | | | |
|---|---|---|---|
| EP | 0 465 913 A2 | 1/1992 | |
| EP | 0 465 913 A3 | 1/1992 | |
| EP | 0 465 913 | 9/1997 | |
| EP | 1 252 889 A1 | 10/2002 | |
| EP | 1 252 889 | 8/2006 | |
| JP | 5 170742 | 7/1993 | |
| JP | 6-135934 | 5/1994 | |
| JP | 11 509548 | 8/1999 | |
| JP | 2004 503586 | 2/2004 | |
| WO | WO 97/03951 A1 | 2/1997 | |

OTHER PUBLICATIONS

Kimura, H., et al., "Synthesis and Antipancreatitis Activities of Novel N-(2-Sulfonylamino-5-trifluoromethyl-3-pyridyl)carboxamide Derivatives as Phospholipase A2 Inhibitors," Chemical & Pharmaceutical Bulletin, vol. 43, No. 10, pp. 1696-1700, (1995).
Marshall, L. A., et al., "SB 203347, an Inhibitor of 14 kDa Phospholipase A2, Alters Human Neutrophil Arachidonic Acid Release and Metabolism and Prolongs Survival in Murine Endotoxin Shock," Journal of Pharmacology and Experimental Therapeutics, vol. 274, No. 3, pp. 1254-1262, (1995).
Hanasaki, K., et al., "Resistance to Endotoxic Shock in Phospholipase A2 Receptor-deficient Mice," Journal of Biological Chemistry, vol. 272, No. 52, pp. 32792-32797, (1997).
International Search Report Issued Jun. 8, 2010 in PCT/JP10/058310 Filed May 17, 2010.
Extended European Search Report issued Oct. 29, 2012, in European Patent Application No. 10780439.5.
Hiroshi Shikama, et al., "Effect of IS-741 on Cell Adhesion between Human Umbilical Vein Endothelial Cells and HL-60 Cells", Biological & Pharmaceutical Bulletin, vol. 22, No. 2, XP-55040471, Jan. 1, 1999, pp. 127-131.
International Search Report Jan. 5, 2012 in PCT/JP10/058310 filed May 17, 2010.

*Primary Examiner* — Nyeemah A Grazier
(74) *Attorney, Agent, or Firm* — Oblon, Spivak, McClelland, Maier & Neustadt, L.L.P.

(57) ABSTRACT

Septic shock is known to lead to, at the end stage, systematic inflammatory reaction syndrome and multiple organ failure (MOF) and cause the patients' death. In both diseases, the patient dies finally of MOF, and the infiltration by inflammatory cells plays a key role for MOF. Thus, development of therapeutic agents for septic shock by suppressing the infiltration by inflammatory cells has been desired.

To provide a therapeutic or preventive agent for shock, comprising as an active ingredient a diaminotrifluoromethylpyridine derivative represented by the formula (I) or its salt:

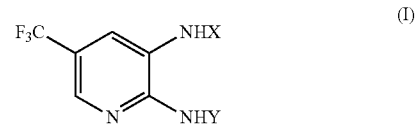

wherein X is a cycloalkylcarbonyl group, an alkenylcarbonyl group, a thiophenecarbonyl group or a benzoyl group which may be substituted by a halogen atom; and Y is an alkylsulfonyl group.

20 Claims, No Drawings

ANTI-SHOCK AGENT COMPRISING DIAMINOTRIFLUOROMETHYLPYRIDINE DERIVATIVE

CROSS REFERENCE TO RELATED APPLICATION

This application is a 371 of PCT/JP2010/058310, filed on May 17, 2010, and claims priority to Japanese Patent Application No. 2009-129578, filed on May 28, 2009.

TECHNICAL FIELD

The present invention relates to an anti-shock agent comprising as an active ingredient a diaminotrifluoromethylpyridine derivative or its salt.

BACKGROUND ART

Patent Document 1 discloses that a diaminotrifluoromethylpyridine derivative or its salt has a phospholipase $A_2$ inhibitory action and is useful as an active ingredient of an anti-inflammatory agent or an anti-pancreatitis agent. It also discloses that (1) phospholipase $A_2$ is secreted or activated in platlets or inflammatory cells by stimulations and contributes to the production of a platlet activating factor (PAF) and arachidonic acid metabolites, (2) the arachidonic acid metabolites are closely related to various diseases, for example, inflammatory symptoms such as rheumatic arthritis, arthritis deformans, tendinitis, bursitis, psoriasis and related dermatitis; nasal and bronchial airway troubles such as allergic rhinitis and allergic bronchial asthma; and immediate hypersensitive reactions such as allergic conjunctivitis, (3) on the other hand, phospholipase $A_2$ secreted from pancreas is activated in the intestine and exhibits a digestive action, but once activated in the pancreas, it is believed to be one of the factors causing pancreatitis, and (4) the above diaminotrifluoromethylpyridine derivative inhibits phospholipase $A_2$ and thus is effective for treatment of diseases related to phospholipase $A_2$ such as inflammatory symptoms, nasal and bronchial airway troubles, immediate hypersensitive reactions or pancreatitis, and can be used as an anti-inflammatory agent, an agent for treating bronchial asthma, an anti-allergy agent, an anti-pancreatitis agent, an anti-nephritis agent or an anti-multiple organ failure agent. Patent Document 2 discloses that acute respiratory distress syndrome (ARDS) which occurs when excessive invasion due to various underlying diseases including various shocks is applied to the body, can be treated or prevented by the diaminotrifluoromethylpyridine derivative or its salt. However, these documents failed to disclose that various shocks can be treated by the diaminotrifluoromethylpyridine derivative or its salt.

PRIOR ART DOCUMENTS

Patent Documents

Patent Document 1: European Patent Publication No. 465913
Patent Document 2: European Patent Publication No. 1252889

DISCLOSURE OF INVENTION

Technical Problem

A shock is considered to be an ischemic disease in a broad sense, and there are various causes such as septic shock, hemorrhagic shock and cardiogenic shock. Septic shock develops in patients with severe Gram-negative infection, and is one of serious diseases which kill the patients in severe cases. There are many patients mainly in the fields of emergency medical care. As an anti-shock agent, steroids and MIRACLID which is one type of protease inhibitors are used. However, the mortality is still high, and more effective agents have been desired.

Septic shock leads to, at the end stage, systematic inflammatory reaction syndrome (SIRS) and multiple organ failure (MOF) and causes the patients' death. In both diseases, in precursor clinical conditions which will result in death, the infiltration by inflammatory cells plays a key role. Thus, development of therapeutic agents for septic shock by suppressing the infiltration by inflammatory cells has been desired.

Solution to Problem

The present inventors have made mouse models with septic shock, the onset of which was peritonitis triggered by the cecal puncture, and conducted studies employing improvement in the survival rate as an index. As a result, they have found that a diaminotrifluoromethylpyridine derivative or its salt is very useful as an anti-shock agent, and accomplished the present invention.

That is, the present invention provides a therapeutic or preventive agent for shock, comprising as an active ingredient a diaminotrifluoromethylpyridine derivative represented by the formula (I) or its salt:

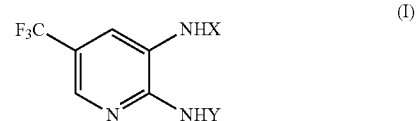

wherein X is a cycloalkylcarbonyl group, an alkenylcarbonyl group, a thiophenecarbonyl group or a benzoyl group which may be substituted by a halogen atom; and Y is an alkylsulfonyl group.

Advantageous Effects of Invention

Various shocks such as septic shock can be treated by suppressing the infiltration by inflammatory cells by a diaminotrifluoromethylpyridine derivative or its salt.

DESCRIPTION OF EMBODIMENTS

In the formula (I), the alkyl moiety contained in Y may, for example, be $C_{1-20}$ alkyl such as methyl, ethyl, propyl, butyl, pentyl, hexyl, heptyl, octyl, decyl or nonadecyl, and they include linear or branched aliphatic structural isomers. The alkenyl moiety contained in X may be $C_{2-20}$ alkenyl such as vinyl, propenyl, butenyl, pentenyl, hexenyl, decenyl or nonadecenyl, and they include linear or branched aliphatic structural isomers. The cycloalkyl moiety contained in X may be $C_{3-8}$ cycloalkyl such as cyclopropyl, cyclobutyl, cyclopentyl, cyclohexyl or cyclooctyl. Further, the halogen atom contained in X may be a fluorine atom, a chlorine atom, a bromine atom or an iodine atom.

Specific examples of the above compounds represented by the formula (I) include N-(2-ethylsulfonylamino-5-trifluoromethyl-3-pyridyl)cyclohexanecarboxamide, N-(2-methylsulfonylamino-5-trifluoromethyl-3-pyridyl)crotonamide, N-(2-methylsulfonylamino-5-trifluoromethyl-3-pyridyl)-2-thiophenecarboxamide, N-(2-methylsulfonylamino-5-trifluoromethyl-3-pyridyl)cyclopentanecarboxamide, N-(2-methylsulfonylamino-5-trifluoromethyl-3-pyridyl)-4-fluorobenzamide, and their salts. Among them, N-(2-ethylsulfonylamino-5-trifluoromethyl-3-pyridyl)cyclohexanecarboxamide is preferred.

The compounds represented by the formula (I) may form a salt. Such a salt may be any pharmaceutically acceptable salt, for example, an alkali metal salt such as a potassium salt or a sodium salt, an alkaline earth metal salt such as a calcium salt, or an organic amine salt such as a triethanolamine salt or a tris(hydroxymethyl)aminomethane salt. Such a salt may have crystal water.

The compounds represented by the compound (I) may be produced, for example, by the method disclosed in European Patent Publication No. 465913. Such compounds may have geometrical isomers depending on the type of a substituent, and such isomers (cis-form and trans-form) and mixtures thereof are included in the present invention.

The compound represented by the formula (I) or its salt is useful as an active ingredient of an anti-shock agent. Various shocks such as septic shock can be treated by suppressing the infiltration by inflammatory cells by the compound represented by the formula (I) or its salt. That is, the infiltration by inflammatory cells plays a key role in the precursor clinical conditions of various shocks such as septic shock, which will result in death. It is considered that by suppressing the infiltration by inflammatory cells, circulatory disorders by the shock are improved. This anti-shock agent is useful to prevent or treat septic shock and multiple organ failure induced thereby, and ischemic diseases in the heart, kidney, liver, stomach and intestines, the brain, etc.

In the case of applying the compound represented by the formula (I) or its salt as an anti-shock agent, it is formulated alone or together with a pharmaceutically acceptable carrier or the like into a drug composition suitable for peroral, parenteral, topical or per rectal administration, such as a tablet, a powder, a capsule, a granule, an injection drug, an ointment, an inhalant or an enema, and it is administered in the form of such a drug formulation.

As a drug formulation suitable for peroral administration, a solid composition such as a tablet, a capsule, a powder, a granule or a troche; or a liquid composition such as a syrup suspension, may, for example, be mentioned. The solid composition such as a tablet, a capsule, a powder, a granule or a troche may contain a binder such as fine crystalline cellulose, gum arabic, tragacanth gum, gelatin or polyvinyl chloride; an excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatin, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95 wt % of the active ingredient compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a medically acceptable oil or liquid). In such a case, it may contain benzyl alcohol as an antibacterial agent, ascorbic acid as an antioxidant, a medically acceptable buffer solution or a reagent for adjusting the osmotic pressure. Such an injection drug preferably contains from 0.1 to 8 wt % of the active ingredient compound.

A drug formulation suitable for topical or per rectal administration may, for example, be an inhalant, an ointment, an enema or a suppository. The inhalant may be formulated by dissolving the compound of the present invention alone or together with a medically acceptable inert carrier in an aerosol or nebulizer solution, or may be administered to the respiratory airway in the form of fine powder for inhalation. In the case of fine powder for inhalation, the particle size is usually not more than 50μ, preferably not more than 10μ. Such an inhalant may be used, if necessary, in combination with other antiasthematic agent or bronchodilator.

An ointment may be prepared by a conventional method by an addition of e.g. a commonly employed base. The ointment preferably contains from 0.1 to 30 wt % of the active ingredient compound.

A suppository may contain a carrier for formulation which is well known in this field, such as polyethylene glycol, lanolin, cacao butter or fatty acid triglyceride. The suppository preferably contains from 1 to 95 wt % of the active ingredient compound.

The above drug compositions suitable for peroral, parenteral, topical or per rectal administration, may be formulated by known methods so that after administration to a patient, the active ingredient will be rapidly discharged, gradually discharged or belatedly discharged.

Needless to say, the dose of the compound represented by the formula (I) or its salt varies depending upon the type of the compound, the administration method, the condition of the patient or the animal to be treated, and the optimum dose and the number of administration under a specific condition must be determined by the judgment of a competent doctor. Usually, however, a daily dose to an adult is from about 0.1 mg to about 10 g, preferably from about 1 mg to about 1 g. In the case of the above inhalation method, the dose of the compound of the present invention is preferably from about 0.01 mg to about 1 g per administration.

Now, specific Formulation Examples of the therapeutic or preventive agent for shock will be given. However, the formulation of the present invention is not limited thereto.

Formulation Example 1

Tablet

| | |
|---|---|
| (1) Active ingredient | 20 mg |
| (2) Lactose | 150 mg |
| (3) Starch | 30 mg |
| (4) Magnesium stearate | 6 mg |

The above composition is tabletted so that the components (1) to (4) constitute one tablet.

Formulation Example 2

Powder, Subtilized Granule or Granule

| | |
|---|---|
| (1) Active ingredient | 20 mg |
| (2) Sugar ester (DK ester F-160, tradename, manufactured by DAI-ICHI KOGYO SEIYAKU CO., LTD.) | 180 mg |
| (3) Surfactant (DECA-GREEN 1-L, tradename, manufactured by Nikko Chemicals Co., Ltd.) | 15 mg |
| (4) Light silicic anhydride | 25 mg |

The above components (1) to (4) are mixed and formed into a powder, or subtilized granule or granule by granulation. Such a powder, subtilized granule or granule may be sealed in a capsule to obtain a capsule drug.

Formulation Example 3

Hard Gelatin Capsule Drug

| | |
|---|---|
| (1) Active ingredient | 25 mg |
| (2) Starch | 200 mg |
| (3) Magnesium stearate | 10 mg |

The above components (1) to (3) are packed in one hard gelatin capsule to obtain a hard gelatin capsule drug.

Formulation Example 4

Injection Drug

| | |
|---|---|
| (1) Active ingredient | 1 mg |
| (2) Glucose | 10 mg |
| (3) Tris(hydroxymethyl)aminomethane | 2.16 mg |

A tris buffer containing the components (1) to (3) is freeze-dried to prepare an injection drug.

Formulation Example 5

Ointment for External Skin Application

| | |
|---|---|
| (1) Active ingredient | 0.5 g |
| (2) White vaseline | 25 g |
| (3) Stearyl alcohol | 22 g |
| (4) Propylene glycol | 12 g |
| (5) Sodium lauryl sulfate | 1.5 g |
| (6) Ethyl parahydroxybenzoate | 0.025 g |
| (7) Propyl parahydroxybenzoate | 0.015 g |
| (8) Purified water | 100 g |

The components (1) to (8) are formulated into an ointment for external skin application by a usual method for preparation of an ointment.

Formulation Example 6

Enema Formulation

| | |
|---|---|
| (1) Active ingredient | 50 mg |
| (2) Macrogol 400 | 2 g |
| (3) Dipotassium phosphate | 141 mg |
| (4) Potassium dihydrogenphosphate | 44 mg |
| (5) Methyl parahydroxybenzoate | 20 mg |
| (6) Purified water | 50 g |

The active ingredient and methyl parahydroxybenzoate are added to Macrogol 400, followed by stirring to obtain a mixture, to which one obtained by adding dipotassium phosphate and potassium dihydrogenphosphate to the purified water is gradually added to prepare an enema formulation.

Formulation Example 7

Suppository

| | |
|---|---|
| (1) Active ingredient | 50 mg |
| (2) Higher fatty acid glyceride | 1,650 mg |

The component (1) is dispersed or dissolved in (2), and packed and sealed in a plastic container having a size appropriate as a suppository, followed by cooling for solidification to prepare a suppository.

Formulation Example 8

Rectum Remaining Suppository, Controlled Release Suppository

| | |
|---|---|
| (1) Active ingredient | 1 g |
| (2) Witepsol W35 | 19 g |

The component (1) is admixed with preliminarily heated and dissolved (2), and the admixture is packed and sealed in a plastic container having a size appropriate as a suppository, followed by cooling for solidification to prepare a suppository.

EXAMPLES

Test Example 1

Therapeutic Effect on Mouse Models with Septic Shock, the Onset of which was Peritonitis Triggered by the Cecal Puncture Therapeutic effects of N-(2-ethylsulfonylamino-5-trifluoromethyl-3-pyridyl)cylohexanecarboxamide sodium salt monohydrate (hereinafter referred to as compound 1) on mouse models with septic shock, the onset of which was peritonitis triggered by the cecal puncture, was examined.

(1) Formulation of Compound 1

The compound 1 was used as a drug formulation. The formulation composition (content per one vial) was as follows.

| | |
|---|---|
| (a) Compound 1 (as anhydride) | 100 mg |
| (b) D-mannitol (manufactured by KYOWA HAKKO KOGYO CO., LTD.) | 100 mg |
| (c) Tris(hydroxymethyl)aminomethane (manufactured by JUNSEI CHEMICAL CO., LTD.) | 21.6 mg |
| (d) Hydrochloric acid (manufactured by SANKYO KAGAKU CHEMICAL CO., LTD. | optimum amount |
| (e) Sodium hydroxide (manufactured by Nippon Rika) | optimum amount |
| (f) Distilled water | 10 ml |
| pH 8.7 ± 0.5 | |

(2) Animal to be Tested

Animal species: mouse

Strain: Crj: BALB/c

Purchased from: Charles River Japan Inc., Atsugi Breeding Center

Sex: female

Age: 7 weeks old when purchased and 8 weeks old when tested

The mice were pre-bred for about a week after purchase and then subjected to a test at about 8 weeks old. Breeding in the entire breeding period was carried out in an isolator placed in a large animal room. Ten mice in each group were accommodated in a polycarbonate cage throughout the test period, and they were freely fed on commercially available complete feed pellet (MF, manufactured by O. B. S.) and tap water subjected to activated carbon filtration (with use of a feed water bottle) throughout the breeding period. From the mice, mice which were healthily grown during the pre-breeding period were selected. Mice were randomly selected from the above selected mice and delivered to the respective groups one by one in the order of the animal number. The animal number was put in the order of put into a cage after the grouping.

(3) Constitution of Animal Group to be Tested

As shown in Table 1, there were groups of treated groups given with 0.1, 1 and 10 mg/kg of the compound 1 and a non-treated group given with a medium (5% glucose), and the number of mice in each group was ten.

TABLE 1

| Group | Administration | Dose mg/kg × 4 times | Number of animals |
|---|---|---|---|
| Non-treated group | 5% glucose | 0 | 10 |
| Treated group at low dose of compound 1 | Compound 1 | 0.1 | 10 |
| Treated group at medium dose of compound 1 | Compound 1 | 1 | 10 |
| Treated group at high dose of compound 1 | Compound 1 | 10 | 10 |

(4) Preparation and Administration of Drug

Preparation of the drug was carried out immediately before the induction operation, and administration was carried out by using the prepared liquid for administration. Japanese Pharmacopoeia 5% glucose was injected to a formulated product containing 100 mg of the compound 1 to completely dissolve the compound 1, and a liquid for administration at the maximum dose was prepared by diluting with Japanese Pharmacopoeia 5% glucose, and a liquid for administration at a medium dose and a liquid for administration at a low dose were prepared by stepwise dilution of the liquid for administration at the maximum dose with Japanese Pharmacopoeia 5% glucose. For the non-treated group, Japanese Pharmacopoeia 5% glucose as a medium alone was prepared. Immediately after the induction, 4 hours later, 8 hours later and 12 hours later, the liquid was repeatedly administered subcutaneously to the dorsal neck to maintain the blood concentration. The liquid was administered in a volume of 10 ml/kg for each group.

(5) Operation to Induce Septic Shock, the Onset of which was Peritonitis Triggered by the Cecal Puncture of Mice Mice were anesthetized with gas-oxygen-fluothane, and the corpus 8 mm from the cecal apex was ligated through an abdominal incision, one spot in the apex was punctured and transfixed with a 22 G needle, and after leakage of cecal contents was confirmed, the cecum was completely replaced in the abdomen and the abdomen was closed.

(6) Test

Viability test was carried out for 3 days from immediately after the induction, and the results were summarized every 24 hours.

(7) Statistical Analysis

Statistical analysis was carried out with respect to the surviving rate. The method is described in detail below.

I. Statistics Application

Carried out by using EXCEL (data counting), SAS (Shirley-Williams), Notepad for Windows 95 (program).

II. Handling of Incomplete Data

When it was possible to exclude data due to experimental technical errors or with a certain definite cause, such data were excluded to carry out analysis. The other data were basically not rejected to carry out analysis. No such cases occurred.

III. Level of Significance and Two-Sided/One-Sided

The level of significance was 5%, and two-sided test was carried out.

IV. Test Technique

Employing the non-treated group as a control, comparison among groups of a group given with 0.1 mg/kg of the compound 1, a group given with 1 mg/kg of the compound 1 and a group given with 10 mg/kg of the compound 1 was carried out.

[Analysis Data]

Viability test results: animals which died in 0 to 24 hours were scored 1, animals which died in 24 to 48 hours were scored 2, animals which died in 48 to 72 hours were scored 3, and animals which survived 72 hours or more were scored 4, and the obtained data were used.

[Test Technique]

Comparison among groups was carried out by Shirley-Williams' multiple comparison test.

(8) Test Results

The results of the test were shown in Table 2. The prepared septic shock model was a model which suffered from peritonitis induced by the cecal puncture and died of septic shock. From the results of this test, improvement in the surviving rate with statical significance (P<0.001) was confirmed with administration of 10 mg/kg.

TABLE 2

| | (surviving rate) | | |
| --- | --- | --- | --- |
| | Time after induction of septic shock model | | |
| Group | 24 hr | 48 hr | 72 hr |
| Non-treated | 20% | 0% | 0% |
| Compound 1; 0.1 mg/kg | 20% | 0% | 0% |
| Compound 1; 1 mg/kg | 40% | 10% | 10% |
| Compound 1; 10 mg/kg | 90% | 50% | 50% |

The invention claimed is:

1. A method for treating shock of a patient or an animal to be treated, which comprises administering an effective amount of a diaminotrifluoromethylpyridine derivative represented by formula (I) or a salt thereof to the patient or the animal to be treated:

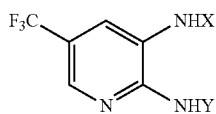

wherein X is a cycloalkylcarbonyl group, an alkenylcarbonyl group, a thiophenecarbonyl group or a benzoyl group which may be substituted by a halogen atom; and Y is an alkylsulfonyl group,
with the proviso that the shock is not one caused by pancreatitus.

2. The method according to claim 1, wherein the shock is hemorrhagic shock.

3. The method according to claim 1, wherein the shock is cardiogenic shock.

4. The method according to claim 1, wherein said diaminotrifluoromethylpyridine derivative represented by formula (I) or a salt thereof is comprised in a composition with a pharmaceutically acceptable carrier.

5. The method according to claim 4, wherein said composition is in the form of a tablet, a powder, a capsule, a granule, an injection drug, an ointment, an inhalant or an enema.

6. The method according to claim 4, wherein said diaminotrifluoromethylpyridine derivative represented by formula (I) or a salt thereof is present in said composition in an amount of from 1 to 95 wt %, relative to the entire weight of the composition.

7. The method according to claim 4, wherein
said composition is in the form of a suspension or an emulsion,
said composition optionally further comprises at least one of benzyl alcohol, ascorbic acid, a medically acceptable buffer solution and a reagent for adjusting the osmotic pressure, and
said diaminotrifluoromethylpyridine derivative represented by formula (I) or a salt thereof is present in the suspension or emulsion in an amount of from 0.1 to 8 wt %, relative to the entire weight of the suspension or emulsion.

8. The method according to claim 4, wherein
said composition is in the form of an ointment that further comprises a base, and
said diaminotrifluoromethylpyridine derivative represented by formula (I) or a salt thereof is present in the ointment in an amount of from 0.1 to 30 wt %, relative to the entire weight of the suspension or emulsion.

9. The method according to claim 4, wherein
said composition is in the form of a suppository,
said pharmaceutically acceptable carrier comprises at least one of polyethylene glycol, lanolin, cacao butter and fatty acid triglyceride, and
said diaminotrifluoromethylpyridine derivative represented by formula (I) or a salt thereof is present in the ointment in an amount of from 1 to 95 wt %, relative to the entire weight of the suspension or emulsion.

10. The method according to claim 4, wherein
said composition is in the form of an inhalant comprised of powder particles having a particle size of not more than 50 μm,
said composition is optionally further comprised of an antiasthematic agent or a bronchodilator, and
said administering comprises inhaling the inhalant by the patient.

11. The method according to claim 4, wherein
said composition is in the form of an inhalant comprised of powder particles having a particle size of not more than 10 μm,
said composition is optionally further comprised of an antiasthematic agent or a bronchodilator, and
said administering comprises inhaling the inhalant by the patient.

12. The method according to claim 11, wherein said effective amount is from about 0.01 mg to about 1 g per administration of the inhalant.

13. The method according to claim 1, wherein said effective amount is a daily dose to an adult of from about 0.1 mg to about 10 g.

14. The method according to claim 1, wherein said effective amount is a daily dose to an adult of from about 1 mg to about 1 g.

15. A method, which comprises administering a therapeutically effective amount of a diaminotrifluoromethylpyridine derivative represented by formula (I) or a salt thereof to a patient in septic shock and in need thereof:

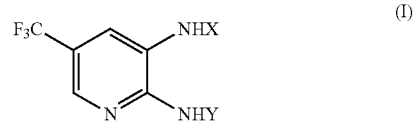

wherein X is a cycloalkylcarbonyl group, an alkenylcarbonyl group, a thiophenecarbonyl group or a benzoyl group which may be substituted by a halogen atom; and Y is an alkylsulfonyl group.

16. The method according to claim 15, wherein the diaminotrifluoromethylpyridine derivative is N-(2-ethylsulfonylamino-5-trifluoromethyl-3-pyridyl)cyclohexanecarboxamide.

17. The method according to claim 1, wherein the diaminotrifluoromethylpyridine derivative is N-(2-ethylsulfonylamino-5-trifluoromethyl-3-pyridyl)cyclohexanecarboxamide, N-(2-methylsulfonylamino-5-trifluoromethyl-3-pyridyl)crotonamide, N-(2-methylsulfonylamino-5-trifluoromethyl-3-pyridyl)-2-thiophenecarboxamide, N-(2-methylsulfonylamino-5-trifluoromethyl-3-pyridyl)cyclopentanecarboxamide or N-(2-methylsulfonylamino-5-trifluoromethyl-3-pyridyl)-4-fluorobenzamide.

18. The method according to claim 1, wherein the diaminotrifluoromethylpyridine derivative is N-(2-ethylsulfonylamino-5-trifluoromethyl-3-pyridyl)cyclohexanecarboxamide.

19. The method according to claim 1, wherein the shock is septic shock, hemorrhagic shock or cardiogenic shock.

20. The method according to claim 1, wherein the shock is septic shock.

* * * * *